US011653992B2

(12) United States Patent
Lenzenhuber et al.

(10) Patent No.: US 11,653,992 B2
(45) Date of Patent: May 23, 2023

(54) PACKAGING HAVING A HOLDING DEVICE FOR HOLDING A MEDICAL TOOL

(71) Applicant: AESCULAP AG, Tuttlingen (DE)

(72) Inventors: Frederick Lenzenhuber, Tuttlingen (DE); Roland-Alois Högerle, Tuttlingen (DE)

(73) Assignee: Aesculap AG

( * ) Notice: Subject to any disclaimer, the term of this patent is extended or adjusted under 35 U.S.C. 154(b) by 264 days.

(21) Appl. No.: 17/271,797

(22) PCT Filed: Sep. 4, 2019

(86) PCT No.: PCT/EP2019/073577
§ 371 (c)(1),
(2) Date: Feb. 26, 2021

(87) PCT Pub. No.: WO2020/049042
PCT Pub. Date: Mar. 12, 2020

(65) Prior Publication Data
US 2021/0338357 A1 Nov. 4, 2021

(30) Foreign Application Priority Data

Sep. 5, 2018 (DE) ..................... 10 2018 121 683.1

(51) Int. Cl.
*A61B 50/00* (2016.01)
*A61B 50/22* (2016.01)
(Continued)

(52) U.S. Cl.
CPC .......... *A61B 50/22* (2016.02); *A61B 50/3001* (2016.02); *A61B 17/1617* (2013.01); *A61B 2017/1602* (2013.01); *A61B 2050/005* (2016.02)

(58) Field of Classification Search
CPC ............... A61B 50/22; A61B 50/3001; A61B 2050/005; A61B 17/1617; A61B 2017/1602
(Continued)

(56) References Cited

U.S. PATENT DOCUMENTS 4,106,621 A 8/1978 Sorenson
4,966,599 A * 10/1990 Pollock .............. A61B 17/8085
606/915

(Continued)

FOREIGN PATENT DOCUMENTS

DE 102005048211 A1 4/2007
DE 202011050118 U1 6/2011
(Continued)

OTHER PUBLICATIONS

German Search Report for German Application No. 10 2018 121 683.1, dated May 20, 2019 with translation, 16 pages. 2019.

(Continued)

*Primary Examiner* — Jacob K Ackun
(74) *Attorney, Agent, or Firm* — RatnerPrestia

(57) ABSTRACT

A holding device for a packaging, more particularly for a sterile packaging, for holding, in a specific location, a medical tool having a tool shaft with a working end, which is to be protected against user-side contact, in a receiving space of the packaging, wherein the holding device has holding means for receiving, in a specific position, the tool, wherein the holding device has a stop for the working end for positioning the tool in the direction of the tool shaft.

15 Claims, 4 Drawing Sheets

(51) Int. Cl.
*A61B 50/30* (2016.01)
*A61B 17/16* (2006.01)

(58) Field of Classification Search
USPC .................................................. 206/363, 370
See application file for complete search history.

(56) References Cited

U.S. PATENT DOCUMENTS

| | | | |
|---|---|---|---|
| 5,108,287 | A | 4/1992 | Yee et al. |
| 5,881,878 | A | 3/1999 | Faccioli et al. |
| 6,273,916 | B1 * | 8/2001 | Murphy ................. A61B 17/70 623/23.62 |
| 9,828,157 | B2 | 11/2017 | Roesler |
| 2015/0283332 | A1 | 10/2015 | Woehr |
| 2021/0338358 | A1 * | 11/2021 | Lenzenhuber ......... A61B 50/30 |

FOREIGN PATENT DOCUMENTS

| | | |
|---|---|---|
| DE | 102013004168 A1 | 9/2014 |
| EP | 3338725 A1 | 6/2018 |
| FR | 2999159 A1 | 6/2014 |
| JP | 2004217289 A | 8/2004 |
| WO | 2017055117 A1 | 4/2017 |

OTHER PUBLICATIONS

English translation of Written Opinion for International Application No. PCT/EP2019/073577, dated Dec. 19, 2019, 6 pages. 2019.

Frank, "Biopolymers—Raw Materials for Innovative Medical Devices" with translation, downloaded at https://www.biooekonomie-bw.de/de/fachbeitrag/aktuell/biopolymere-rohstoffe-fuer-innovative-medizinprodukte, 2016, 9 pages.

Japanese Office Action for Japanese Application No. 2021-512441, dated Aug. 10, 2021, with translation, 14 pages.

International Search Report and Written Opinion for International Application No. PCT/EP2019/073577, dated Dec. 19, 2019, 8 pages.

* cited by examiner though the main application is in surgical tools of the shaft type as defined above.

PACKAGING HAVING A HOLDING DEVICE FOR HOLDING A MEDICAL TOOL

This application is a U.S. National Phase application of PCT International Application No. PCT/EP2019/073577, filed Sep. 4, 2019, which claims the benefit of German Application DE 10 2018 121 683.1, filed Sep. 5, 2018, both of which are incorporated by reference herein.

TECHNICAL FIELD

The present invention relates to a package, in particular a sterile package, comprising a holding device for positionally determined holding of a medical tool of the shaft type having a tool shaft with a working end/effector to be protected from user contact in a receiving space of the package and an outer packaging forming the receiving space for the holding device and the tool held therein, wherein the holding device has holding means/a holding structure for positionally determined receiving/storage of the tool.

BACKGROUND

Various packages and devices for medical products and in particular tools are known. Packages of medical products such as implants and tools with pointed and/or sharp working ends, for example in the form of cutting or sawing edges, milling heads and drills or thread portions, are subject to special requirements. In addition to protecting users from injury before and in particular after use of the tool, it is also necessary to protect the packaged tool from undesirable influences such as contamination and damage. In particular, it has to be ensured that working ends of the tool that come into contact with a patient, which are usually sharp-edged, are not touched by the user. Although it is frequently pointed out in instructions for use that contact with the working ends must be avoided at all costs, it can happen all too easily in normal surgical procedures that the user, for example a surgeon or medical support staff, nevertheless accidentally touches the working ends of tools, blades and the like when inserting them into a handle, a carrier part or a drive unit for the tool. On the one hand, this can result in damage to protective clothing, such as rubber gloves, which may go unnoticed, thus posing a significant risk to the user. On the other hand, the working end of the tool can become contaminated with foreign particles, which in turn involves a considerable risk for the patient.

Packages in which the medical tool is held firmly and/or in a defined position are known from the prior art. An example of such a package is a blister packaging with a clamp in the coupling area of the tool in order to position and hold it in a defined position in the package. Such a package is disclosed, for example, in DE 10 2013 004 168 A1, in which the surgical tool is packaged under sterile conditions in a plastic package, the package is made up of at least two parts and consists of an inner protective packaging for sensitive parts of the surgical tool and a sealable blister packaging that accommodates the protective packaging. Furthermore, a method for packaging sterile surgical tools is proposed in which the surgical tool is packaged in the plastic packaging under sterile conditions, wherein in a first step the surgical tool is first packaged at least partially and in particular with its sensitive cutting edges and working surfaces in the first protective packaging and the protective packaging is transferred together with the surgical tool packaged there into a second blister packaging, where it is secured in position and then sealed with a sealing film. The disadvantage of this packaging is that although the operative edges of the tool are very well protected, the tool, however, may contact the inner protective packaging when it is introduced into a handle and can thus be contaminated.

Known holding devices of packages do not reliably prevent contact with the working ends. A further disadvantage is that further aids or tools are required to insert the tool into handpieces or drive units if direct contact of the user with the tool is to be prevented, which significantly complicates handling.

SUMMARY

Against this background, the present invention is based on the object of reducing the aforementioned disadvantages of the prior art, in particular to provide a package for a medical tool of the shaft type with which it is possible to handle the tool easily and safely, in particular when the tool is inserted into a handle or a drive unit, and with which the risk of contamination of the tool and, in particular, of its working end and, at the same time, the risk of injury to users can be minimized.

This object is solved according to the present invention by a package according to claim 1, i.e. a package, in particular a sterile package, comprising a holding device for positionally determined holding of a medical tool having a tool shaft with a working end to be protected from user contact in a receiving space of the package and an outer packaging forming the receiving space for the holding device and the tool held therein, wherein the holding device comprises holding means for positionally determined receiving of the tool and a stop for the working end for positioning the tool in the direction of the tool shaft.

In other words, the present invention provides a tool accommodation or tool support adapted and provided to be received in a sterile package. The tool support has at least one, preferably several (axially) spaced shaft receiving clamps (each consisting of two resilient/resiliently-mounted clamping arms/clamping jaws) which is/are arranged on a footing or base plate, preferably in one piece of material, and which preferably each forms at least one or more bulging portions for accommodating a tool shaft in a (partially) surrounding manner.

In order to prevent axial movement of the tool/tool shaft in the tool accommodation clamp(s), two (axially) spaced end stops are provided, of which preferably at least one end stop is manufactured as a separate component and can be mounted at different positions on the base plate for adaptation to different shaft lengths. It is particularly advantageous that at least one end stop, preferably the separate end stop, consists of a resorbable material or parts thereof consist of resorbable material.

A tool in the sense of the invention is in particular understood to be an operation tool/surgical tool with a generally distal, sharp-edged working ends for performing an operative function and a proximal coupling portion/coupling structure for coupling the tool with a handle unit/handle, in particular a drive handle unit. Examples of such tools are, in particular, rotating tools as well as sawing tools, including drills, milling cutters, saws, screw adapters, cutting blades or grinding adapters, which are coupled to a handle and/or drive unit in a generally known manner. Furthermore, a tool in the sense of the invention is understood to be a spray nozzle, an HF syringe, an ultrasonic blade, etc. Finally, the term 'tool' in the sense of the invention also includes implants of any type and shape, such as bone and joint implants or partial implants, stents, etc., which are coupled to a handling means upon removal from the holding device. Operative portions of such implants, such as threaded portions or the like, constitute the working end in the sense of the invention.

It is a particular advantage of the invention that the holding device comprises a stop defining the position of the tool in the direction of its shaft, i.e. in the direction from the proximal coupling structure to the distal working end. The stop has an abutment surface against which the working end of the tool abuts or comes to abut when it is removed from the holding device. Thus, even when the tool is removed from the holding device by the user, it is orientationally positioned in this direction or fixed by abutment with the stop and can be inserted into and coupled with a handle or a drive unit without having to be additionally held by the user. Furthermore, the working end of the tool to be protected from user contact is covered by the stop, so that the risk of injury is minimized. Particularly good coverage of the working end can be achieved if the stop projects beyond the working end on all sides. It can therefore also be said that the invention ensures that the working end of the tool can only be touched by the stop during the coupling process with a handle.

Advantageous configuration examples of the invention are claimed in the dependent claims and are explained in more detail below.

According to one embodiment, the stop can consist at least partially or in sections of a resorbable material, preferably it consists entirely of a resorbable material. This has the advantage that the working end of the tool can rest against the stop during a coupling process with a handle or a drive unit without bio-incompatible material being rubbed off, adhering to the tool and being inadvertently introduced into the body of a patient. It can also be said that in this way it is ensured that the tool only contacts resorbable material during the coupling process and adhesion of resorbable material is not critical. The resorbable material in the sense of the invention may be a resorbable biopolymer or copolymer thereof, in particular a resorbable polyester, gelatin, thermoplastic starch (TPS) or compositions or mixtures thereof. Preferably, the resorbable material used in the sense of the invention is a polyactide (PLA), in particular a polyactide of the chemical formula (C3H4O2)n-O—CO—CH(CH4), in particular a poly-L-lactide (PLLA), a poly-D-lactide (PDLA) or a poly-DL-lactide (PDLLA), PCL (poly-caprolactane), PHB (polyhydroxybutyric acid) or a composition or mixture of the preceding materials. These resorbable materials not only ensure controllable and safe biodegradation in the body, but are also highly tissue compatible. In the case of PLA, water present in the patient's body breaks down the polymer chains of this material and the human metabolism ultimately converts the D-lactides and L-lactides into carbon dioxide and water, so that particles of material accidentally introduced into the patient's body are degraded in a particularly advantageous manner without leaving any residue. It is within the scope of the invention that the entire holding device is partially or completely made of a resorbable material.

According to a further embodiment, the stop is formed separately from the holding device. In particular, it can be arrangeable or arranged in a plurality of different positions on the holding device, in particular in different positions in the direction of the tool shaft. In this way, the invention can provide a holding device that can be easily adjusted to the respective length of the tool to be arranged therein and can thus be used in a highly flexible manner for different tools with different geometries.

A further embodiment of the invention is characterized in that it comprises a further stop for a coupling structure of the tool opposite the working end. This further stop may also be referred to as a proximal stop (the first stop may be referred to as a distal stop) and serves to position the tool in the direction of the tool shaft, in particular in the proximal direction. It covers the coupling structure and may project beyond it on all sides, so that the coupling structure is particularly well protected. The further stop can advantageously be connected to the holding device by means of a predetermined breaking point. By breaking the predetermined breaking point, it can be easily separated from the holding device and removed so that the coupling structure of the tool is accessible for coupling with a handle or a drive unit after removal of the further stop.

The holding device can comprise a base plate. In particular, this can be designed in such a way that it forms a footprint for position-stable placement of the holding device with a tool held therein, in particular in a state unpacked from the package, and/or an abutment structure for abutment against the package. In addition to the footprint, the holding device may have further abutment structures or portions that interact with and abut on the package so as to ensure clear and stable orientation positioning in the receptacle of the package.

According to a configuration example of the invention, the holding device can have at least two holding structures spaced apart from each other for orientation-determined positioning of the tool. Preferably, each of these is arranged on the base plate and may extend therefrom into the receiving space. In addition to the function of holding the tool, the holding structures can form attachments with which the holding device rests against the package, preferably in such a way that its orientation is secured or fixed in the receptacle of the package. One of the holding structures can be arranged at the end side of the holding device, in particular at the base plate. Another one of the holding structures can be arranged substantially centrally on the holding device, in particular on the base plate. This enables particularly stable holding of the tool in the holding device.

Preferably, one of the holding structures is designed to position the tool in an orientation-determined manner relative to the holding device in a first direction. The other one of the holding structures can be designed to position the tool in an orientation-determined manner relative to the holding device in a second direction and a third direction, wherein the first, second and third directions are orthogonal to each other. By means of such guiding the tool is held stably in the holding device on the one hand, and on the other hand it can be arranged in the holding device and removed from the holding device particularly easily by a user. It is particularly advantageous if, according to a further configuration example of the package, at least one of the holding structures forms a form fit and/or a force fit with the tool, in particular with a coupling structure of the tool.

At least one of the holding structures, in particular both holding structures, can have two holding arms opposite each other. A slit is formed between each of these to receive and hold the tool. The holding arms can be arranged essentially perpendicular to the base plate of the holding device. In a particularly advantageous manner, they can be designed as clamping arms and in particular have resilient properties in a direction transverse to the slit. Removal and arrangement of the tool in the holding structures is particularly easy if, according to one form of the invention, the slit widens in the direction from proximal of the base to distal of the base. This favors largely risk-free handling of both unused and used instruments, so that in particular injury-free disposal of tools in the holding structure is improved and the risk of infection which exists in principle is reduced. According to a further developed embodiment of the invention, the sides of the holding arms facing the slit may be provided with indentations. Such indentations can advantageously form locking pockets for the tool inserted in the slit, so that the tool is held securely in the holding structures and yet can be easily removed by a user.

A particularly user-friendly configuration example of the invention, which avoids injuries of a user by the tool held in the holding device, provides that the holding device comprises a protective lug which protrudes from the base plate into the receiving space and covers a distal end of the tool or a sharp-edged structure of the tool without contact. In this way, a user is protected from injury from any sharp edges of the tool when handling the holding device with the tool held therein.

A further embodiment is characterized in that a plurality of spaced recesses are formed in the base plate and the stop for the working end has a matching pin, so that the stop can be arranged in different positions on the base plate by inserting the pin into one of the recesses. This advantageously enables the holding device to be easily adjusted to different tool geometries.

One embodiment of the invention is characterized in that the holding device is arranged and/or held in a positionally determined manner in the receiving space. In particular, it serves to hold the tool, in particular to hold it in a positionally determined manner and to position it in the receiving space in such a way that the sharp working ends are prevented from coming into contact with the packaging material and that they are spaced from the package. By providing such a holding device, contact of the tool with parts of the package can be prevented or at least safely minimized, so that abrasion of packaging material by the tool can be prevented. The outer packaging may further be made at least partially, preferably entirely, of a resorbable material. The receiving space can be formed to be closed by the outer packaging, in particular to be hermetically sealed. It can also be designed to be sterile.

According to one embodiment of the invention, the holding device is formed separately from the outer packaging. Therefore, the tool held in the holding device can be removed together with the latter from the outer packaging and, in particular, can remain in the holding device even after unpacking until final use. Preferably, the package and holding device are configured such that removal can be accomplished by handling the holding device and without directly contacting the tool, so that the likelihood of contamination of the tool can be easily and safely minimized, or even avoided altogether. In addition, the tool together with the holding device can be placed on an instrument table without having to place it loosely. During an operation or treatment, the holder can be used in a particularly advantageous manner for intermediate storage of the tool, resulting in better order and clarity. In addition to the package in the actual sense, the invention can thus provide an independent holder by means of the separate holding device, which, in addition to safe and stable storage of tools during transport in the respective outer packaging, also enables a possibility for defined positioning and safe handling of the tool during processing (e.g. sterilization) as well as during preparation of the tool during treatment in the operating room. For this purpose, the holding device can be removed from the outer packaging together with the tool held therein and can be set up.

The outer packaging can in particular be formed as a blister. Such blisters are inexpensive and can be manufactured for almost any shape of the tool and/or holding device. Preferably, the blister packaging may have a lower shell with a depression forming the receiving space for the tool. Such a lower shell can simply be formed with a stability and shape sufficient for the orientation-stable positioning of the holding device and tool. By means of a lid foil arranged on the lower shell in a known manner, the receiving space can be closed in the desired manner, in particular hermetically and/or in a sterile manner.

According to a further configuration example of the invention, the package may comprise a carrier element, for example in the form of a sieve basket. It can be arranged in the package together with the holding device and the tool held thereon, in particular with a plurality of holding devices with the respective tool held thereon. By means of such a carrier element, several holding devices with tools held therein can be handled particularly easily and simultaneously, for example, they can be sterilized and/or placed on an instrumentation table.

According to a further configuration example of the invention, the holding device can be coded, for example by having a colored design. In this way, the invention can in an especially simple way provide a system with which not only different tools can be coded in a way that can be easily distinguished by a user, but also such coding or marking of certain tools can be retained even after the tool has been unpacked from the package and assigned to the respective tool. In particular, tools that have already been unpacked and are ready for use on an instrumentation table or in a sterilization facility can be identified particularly easily and reliably by the user. Different tools and/or holding devices can preferably be identified by means of different colors of the holding devices, for example with regard to their indication or to specific product groups, etc. In this way, incorrect combinations can be avoided. In this way, incorrect combinations of tools can be avoided by the coloring of the holding device, which is designed in particular as a plastic injection-molded part, in and outside the package.

According to a further configuration example of the invention, the holding device may be formed as a molded plastic part. If, according to a further developed embodiment of the invention, it is formed as a multi-component injection molding, it can, for example, be provided with a particularly good anti-slip footprint. This enables a stable arrangement of the holding device on an instrument table and/or on a carrier element such as a sieve basket during a processing operation. In addition, this can greatly facilitate the handling of the holding device when removing the unused tool as well as when inserting a used tool.

In summary, it can be said that the invention provides a tool holder or working-end holder which ensures safe and stable support of working ends during transport in the respective outer packaging. When it is prepared, in particular during the coupling process, it is ensured that the working ends are only touched by resorbable material. In particular, the invention brings about the following advantages:

The holding device/package provides a high level of safety for a user.

The holding device/package is very compact

The holding device/package offers very good positional security

Cross-contamination can be prevented with a very high level of safety

BRIEF DESCRIPTION OF DRAWINGS

Further features and advantages of the present invention will be apparent from the following exemplary and non-limiting description of the invention by means of figures. These are merely schematic in nature and serve only for understanding the invention. They show.

DETAILED DESCRIPTION OF EXEMPLARY EMBODIMENTS

Figure 1:
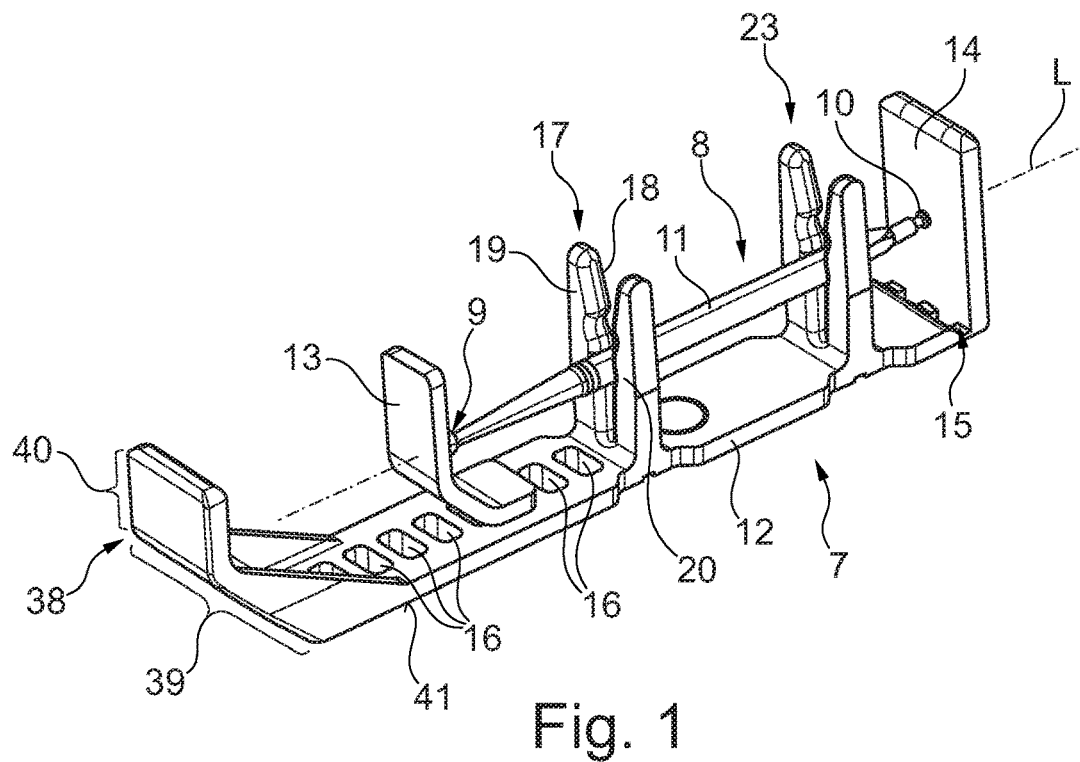
FIG. 1 shows a perspective view of a configuration example of a holding device according to the invention with a tool held therein.

FIG. 1 shows a holding device 7 according to the invention with a tool 8 arranged therein. The tool 8 in the present embodiment is a drill 8, at the distal end of which a working end 9 in the form of a drill head 9 is formed and at the proximal end of which a coupling structure 10 is formed for arranging the tool 8 in a tool reception 26 of a drive handle unit 27. The tool 8 has an elongated tool shaft 11 between the working end 9 and the coupling structure 10.

The holding device is designed as a molded plastic part and has a base plate 12. A first holding structure 17 is formed in the center of the base plate 12. This holding structure 17 comprises two opposite holding arms 19, 20, which form a receiving slit 18 for the tool shaft 11 between them and are parallel to each other, both of which are arranged essentially orthogonally to the base plate 12. Adjacent to the first retaining structure 17, a second retaining structure 23 is formed which is substantially similar to the first retaining structure 17 and is therefore not described further.

Figure 8:
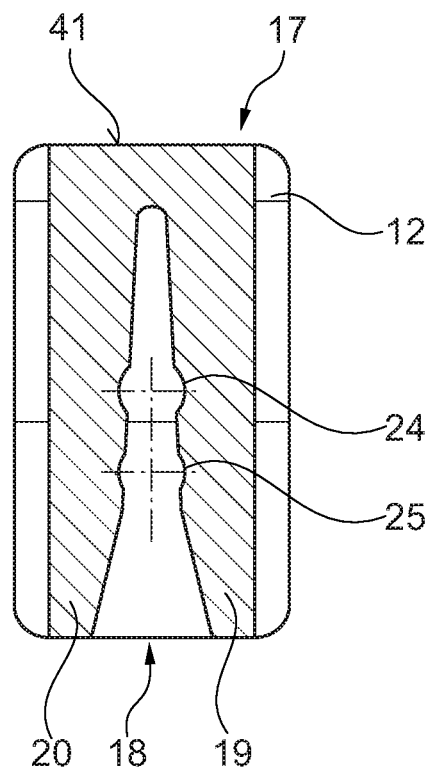
FIG. 8 shows a sectional view of the holding device in a direction transverse to the longitudinal axis.

A protective lug 38 is disposed on the distal (working end-side) end of the base plate 12. The protective lug 38 first projects from the base plate 12 with an inclined portion 39 at an oblique angle (here of about 45°) and is then bent by another angle to an end portion 40, so that its end facing away from the base plate 12 is arranged approximately transversely to the latter. As shown in particular in FIG. 8, the protective lug 38 projects from the base plate 12 to such an extent that the respective distal end of the working end 9 is covered without contact. This configuration of the protective lug 38 creates a good grip possibility in the form of the inclined portion 39 for grasping by a user, wherein the working end 9 is covered so that contact with the user can be reliably prevented and thus the risk of injury can be minimized.

Several continuous recesses 16 are formed in the base plate 12 between the first retaining structure 17 and the distal protective lug 38. These recesses 16 serve to receive and position a stop 13, which engages with a pin (not shown in the figures) in a form-fitting and/or force-fitting manner in one of the recesses 16 and is thus fixed to the base plate 12. The stop 13 consists entirely of a resorbable material and forms an abutment for the working end 9 of the tool 8, by means of which the latter is positioned in the direction of the longitudinal axis L of its tool shaft 11. At the proximal (coupling structure-side) end of the base plate 12, a further stop 14 is arranged thereon in a material-fitting manner by means of a predetermined breaking point 15. The further stop 14 forms a cover for the coupling structure 10 of the tool 8.

Figure 6:
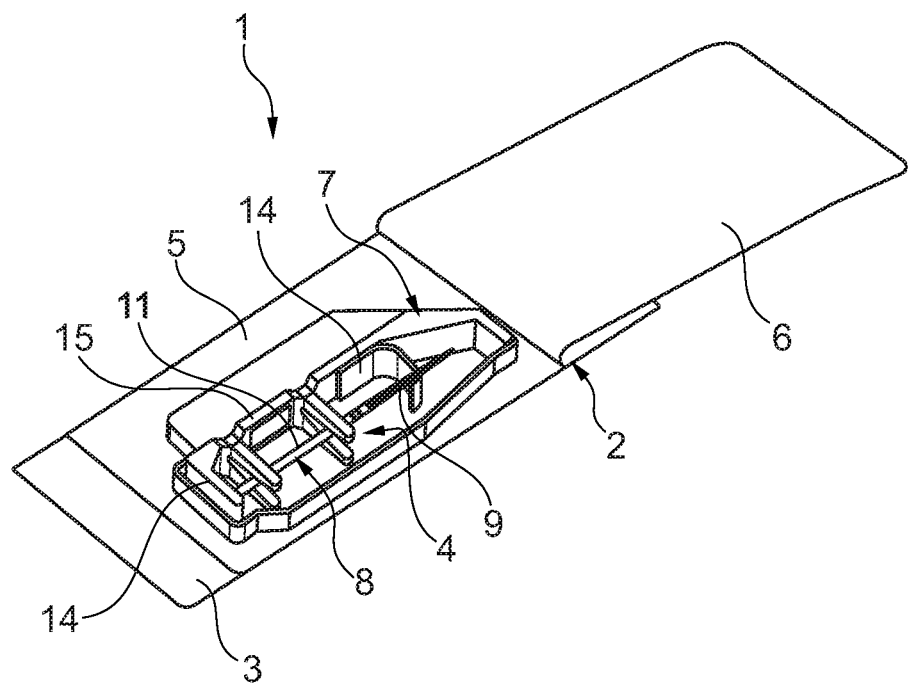
FIG. 6 shows a perspective view of a package according to the invention.
Figure 7:
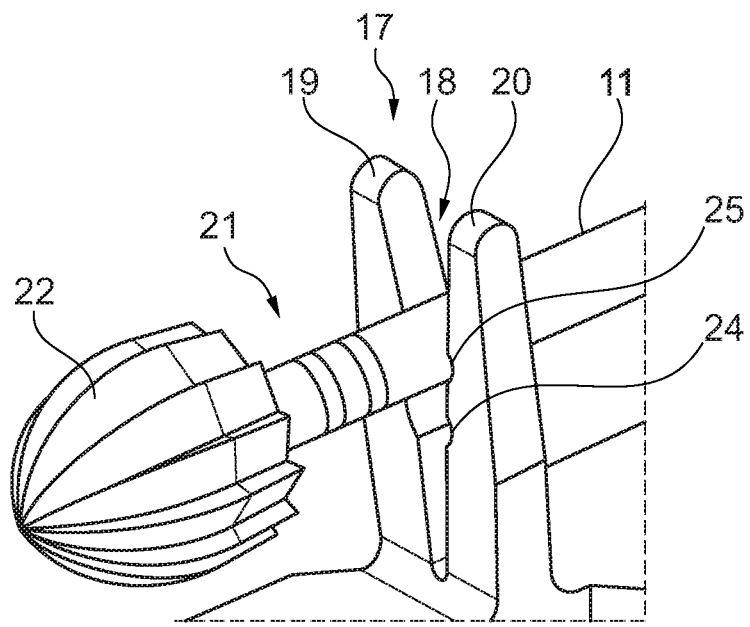
FIG. 7 shows an enlarged detailed view of the holding device.

FIG. 7 shows the holding structure 17 of the holding device 7 in an enlarged detailed view with another tool 21, here in the form of a milling adapter 21. Like the drill 8 of FIGS. 1 to 6, the milling adapter 21 has a coupling structure 10 and a tool shaft 11 and differs from the drill 8 in that its distal working end 22 is in the form of a milling head 22. Nevertheless, the invention allows the drill 8 and the milling head 21 to be accommodated in the same holding devices 7. The side surfaces of the holding arms 19, 20 facing each other are each provided with two indentations 24, 25 of different sizes arranged one above the other, each for receiving tool shafts 11 of different diameters (see also FIG. 8, which shows the second holding structure 17 in a sectional view transverse to the longitudinal axis of the tool 8, 21). The holding arms 19, 20 have certain elastic spring properties and can perform a spring movement relative to each other, so that the slit 18 can widen when a tool 8, 21 is inserted and the holding arms 19, 20 spring back to their original position as soon as the shaft 11 of the corresponding tool 8, 21 is arranged in the indentation 24, 25. In this way, the tool 8, 21 is held securely in the holding device 7. In particular, it can be held clamped between the holding arms 19, 20.

Figure 3:
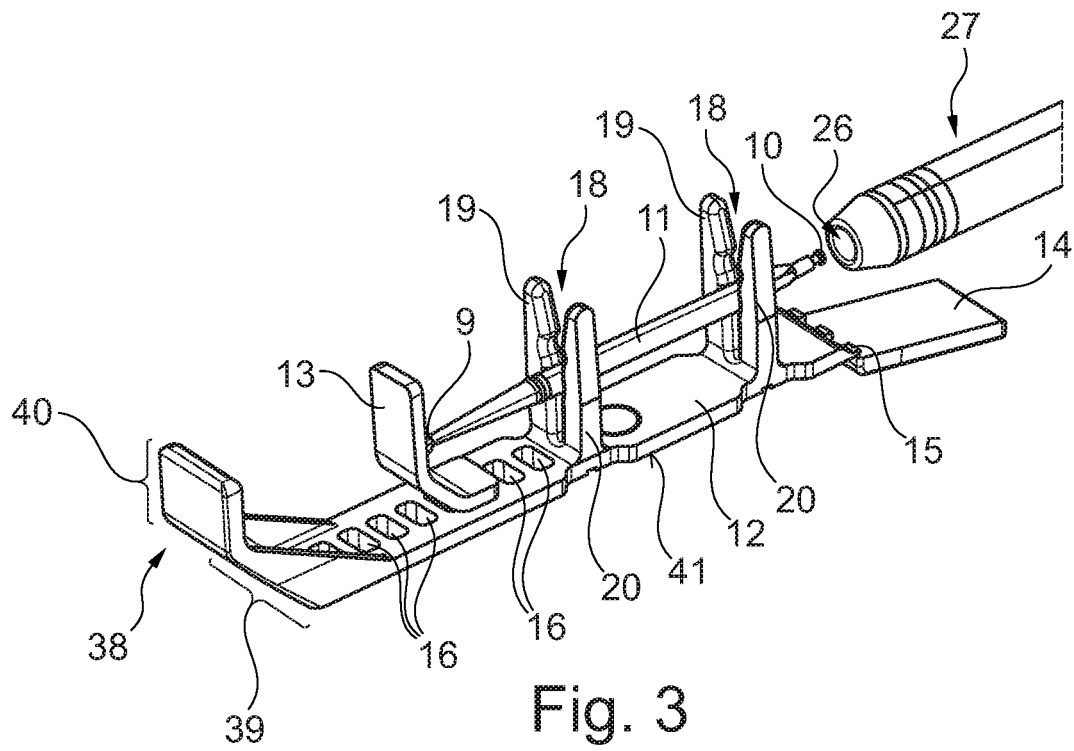
FIG. 3 shows a perspective view of the holding device of FIGS. 1 and 2 during coupling of the tool held therein.

FIG. 6 shows a configuration example of a package 1 according to the invention. It comprises an outer packaging 2 in the form of a blister 2 with a lower shell 3 with a depression 4 formed therein and an edge 5 surrounding the depression 4. The outer packaging 2 further comprises a lid foil 6 which is arranged on the surrounding edge 5 of the lower shell 3 and hermetically seals the depression 4 and which is shown in FIGS. 1 and 3 in each case in a partially opened state. A holding device 7 according to the invention with a tool 8 held therein is arranged in the depression 4 of the outer packaging 2 of FIG. 1 as an example of a packaged product.

The holding device 7 is suitable for receiving and holding different tools 8, 21 as long as they have a substantially similar basic shape with a shaft 11 and a coupling structure 10 at the proximal end and actually differ only with respect to their respective working ends 9, 22. Furthermore, in addition to fixing the position of the tool 8, 21 in the packaged state, i.e. in the state shown in FIG. 6, the holding device 7 can be used as a holding device which can be used separately from the outer packaging 2, in order to set down the tool, for example when it is provided in the course of an operation or during sterilization. The lower side 41 of the base plate 12, 30 forms a footprint 41 for this purpose, on which the holding device 7 with a tool held therein can be placed in a stable manner.

Figure 2:
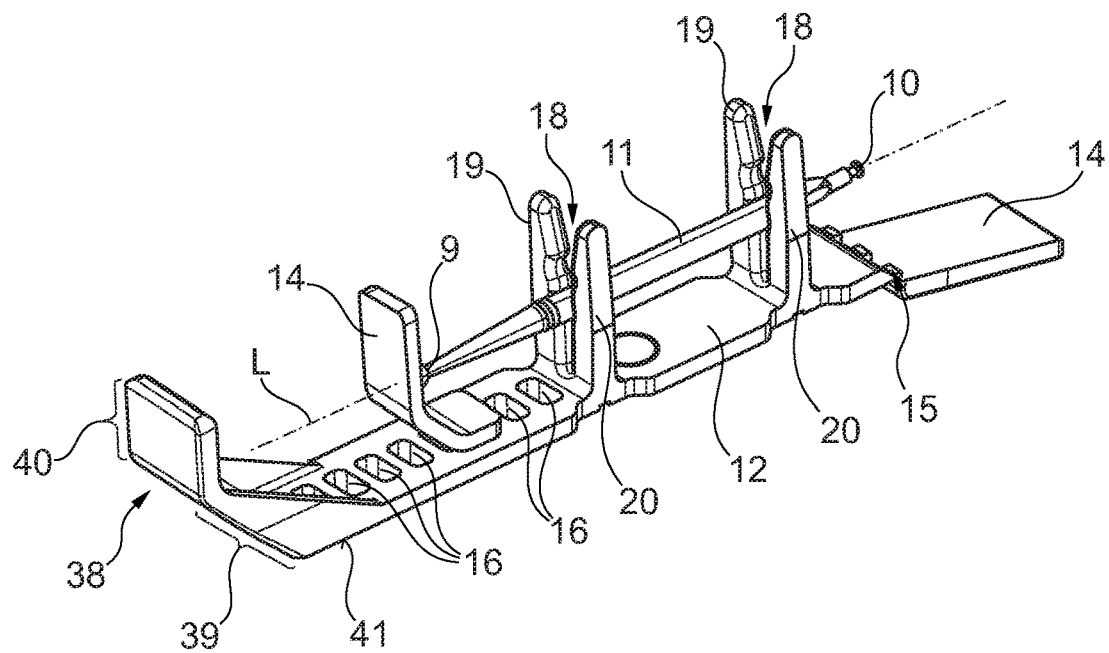
FIG. 2 shows a perspective view of the configuration example of FIG. 1 prepared for coupling the tool.
Figure 4:
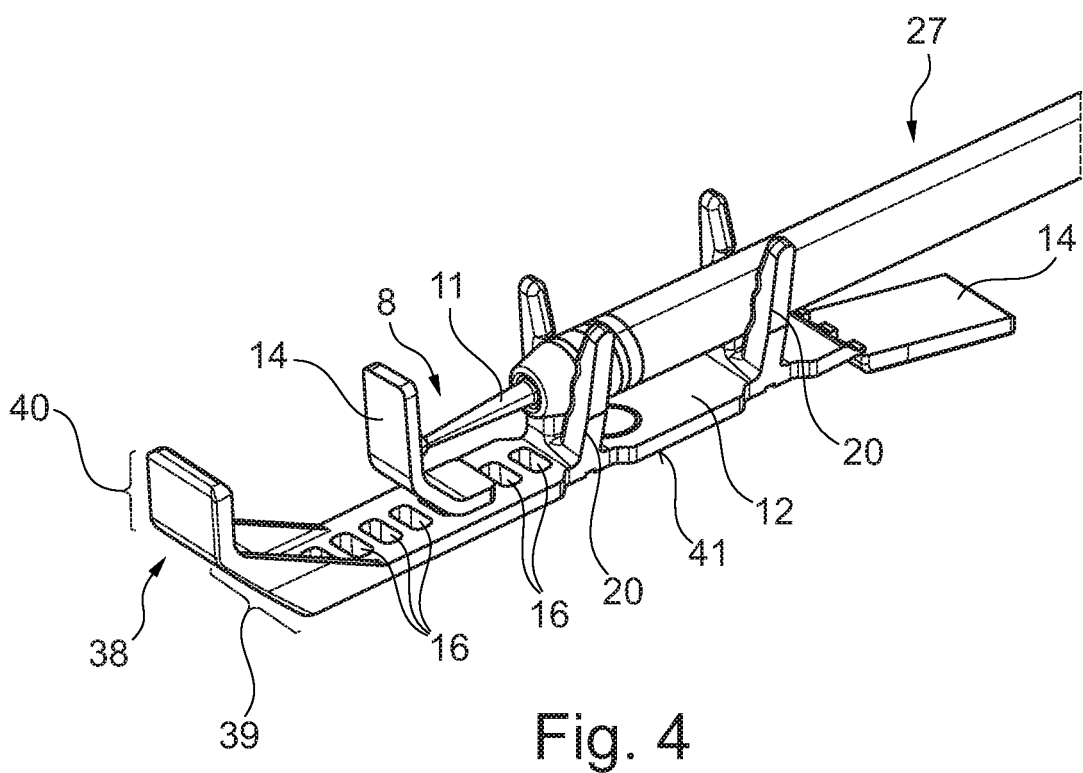
FIG. 4 shows a further perspective view of the holding device of FIGS. 1 and 2 during coupling of the tool held therein.
Figure 5:
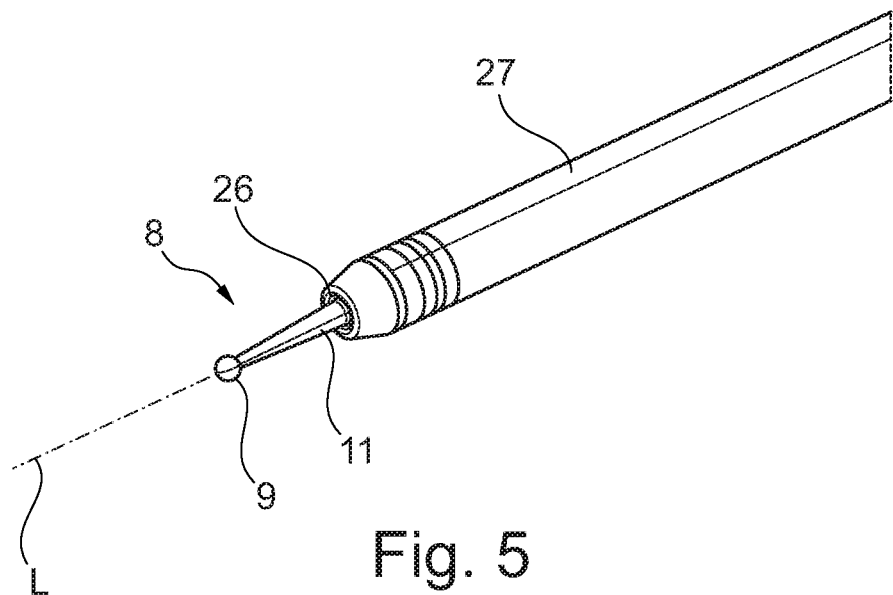
FIG. 5 shows a perspective view of the tool coupled to a handle.

FIGS. 1 to 5 illustrate the use of the holding device 7 in the course of inserting the tool 8 into the tool accommodation 26 of a handle unit 27. FIG. 1 shows the holding device 7 with the tool 8 held therein in the original, packaged state. In this case, the working end 9 rests against the stop 13 so that the tool 8 is fixed in position in the direction of the longitudinal shaft axis L and in particular cannot be displaced in the distal direction, i.e. in the direction of the stop 13. FIG. 2 shows the holding device in the further course of tool removal. The further proximal stop 14 has been snapped off with breaking of the predetermined breaking point 15, so that the proximal coupling structure 10 of the tool is released and accessible for coupling with the tool accommodation 26. FIG. 3 shows how the handle 27 is moved from the proximal direction to the coupling structure 10. Finally, FIG. 4 shows the further course of the coupling, wherein the handle piece 27 has been further inserted into the holding device 7 in the distal direction. In the process, the holding arms 19, 20 of both holding structures 17, 23 deflect outward. At the same time, the working end 9 of the tool 8 is pressed against the stop 13, which is made of a resorbable material, and cannot move in the distal direction. After complete engagement of the coupling structure 10 in the tool accommodation 26, the tool 8 is removed from the holding device 7.

LIST OF REFERENCE SIGNS 1 package
2 package/outer packaging
3 lower shell
4 depression, receiving space
5 edge
6 foil lid
7 holding device
8 tool, drill adapter
9 working end, drill head
10 coupling structure
11 tool shaft
12 base plate
13 stop, distal stop
14 further stop, proximal stop
15 predetermined breaking point
16 recess
17 holding structure
18 receiving slit
19 holding arm, clamping arm
20 holding arm, clamping arm
21 tool, milling adapter
22 working end, milling head
23 holding structure
24 indentation
25 indentation
26 tool accommodation
27 drive handle unit
38 protective lug
39 inclined portion
40 end portion
41 footprint

The invention claimed is:

1. A package comprising:
a holding device for positionally determined holding of a medical tool comprising a tool shaft having a working end to be protected from user contact in a receiving space of the package, and
an outer packaging forming the receiving space for the holding device and the tool held therein,
wherein the holding device has:
holding means configured to receive the tool in a positionally determined manner, and
a stop for the working end for positioning the tool in a direction of the tool shaft,
and wherein
the stop consists at least partially or in section of a resorbable material.

2. The package according to claim 1, wherein the stop consists completely of a resorbable material.

3. The package according to claim 1, wherein the stop is formed separately from the holding device.

4. The package according to claim 1, wherein the package comprises a further stop configured to couple a structure of the tool opposite the working end for positioning the tool in the direction of the tool shaft.

5. The package according to claim 4, wherein the further stop is connected to the holding device by means of a predetermined breaking point and can be removed from the holding device by breaking the predetermined breaking point.

6. The package according to claim 1, wherein the holding device has a base plate which forms a footprint for positionally stable placement of the holding device with a tool held therein.

7. The package according to claim 6, wherein the holding means comprises at least two holding structures spaced apart from each other for positionally-determined positioning of the tool in a direction transverse to the tool shaft.

8. The package according to claim 7, wherein at least one of the holding structures has two opposite holding arms, between which a slot is formed for receiving and holding the tool.

9. The package according to claim 6, wherein a plurality of spaced recesses is formed in the base plate and the stop for the working end has a matching pin, so that the stop can be arranged in different positions on the base plate by inserting the pin into one of the plurality of spaced recesses.

10. The package according to claim 1, wherein the outer packaging is designed as a blister, having a lower shell which has a depression forming the receiving space, and with a lid foil arranged thereon and closing the receiving space.

11. The package according to claim 1, wherein the stop can be arranged in a plurality of different positions on the holding device.

12. The package according to claim 11, wherein the stop can be arranged in a plurality of different positions in the direction of the tool shaft.

13. A package comprising:
a holding device for positionally determined holding of a medical tool comprising a tool shaft having a working end to be protected from user contact in a receiving space of the package, and
an outer packaging forming the receiving space for the holding device and the tool held therein,
wherein the holding device has holding means for receiving the tool in a positionally determined manner and a stop for the working end for positioning the tool in the direction of the tool shaft,
and wherein
the stop consists completely of a resorbable material.

14. A package comprising:
a holding device for positionally determined holding of a medical tool comprising a tool shaft having a working end to be protected from user contact in a receiving space of the package, and an outer packaging forming the receiving space for the holding device and the tool held therein, wherein the holding device has holding means for receiving the tool in a positionally determined manner and a stop for the working end for positioning the tool in the direction of the tool shaft, and wherein the stop is formed separately from the holding device.

15. A package comprising:

a holding device for positionally determined holding of a medical tool comprising a tool shaft having a working end to be protected from user contact in a receiving space of the package, and an outer packaging forming the receiving space for the holding device and the tool held therein, wherein the holding device has holding means for receiving the tool in a positionally determined manner and a stop for the working end for positioning the tool in the direction of the tool shaft, and wherein the stop can be arranged in a plurality of different positions on the holding device.

* * * * *